United States Patent
Poyet et al.

(10) Patent No.: US 10,463,713 B2
(45) Date of Patent: *Nov. 5, 2019

(54) USE OF AAC-11 INHIBITORS FOR THE TREATMENT OF VIRAL INFECTION

(71) Applicants: INSERM (Institut National de la Sante et de la Recherche Medicale), Paris (FR); Universite Paris Diderot-Paris 7, Paris (FR); Institut Pasteur, Paris (FR)

(72) Inventors: Jean-Luc Poyet, Paris (FR); Asier Saez-Cirion, Paris (FR); Heriberto Bruzzoni-Giovanelli, Paris (FR); Leonard Jagot-Lacoussiere, Paris (FR); Annie David, Paris (FR); Anastassia Mikhailova, Paris (FR)

(73) Assignees: INSERM (INSTITUT NATIONAL DE LA SANTE ET DE LA RECHERCHE MEDICALE), Paris (FR); UNIVERSITE PARIS DIDEROT-PARIS 7, Paris (FR); INSTITUT PASTEUR, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/075,224

(22) PCT Filed: Feb. 3, 2017

(86) PCT No.: PCT/EP2017/052448
§ 371 (c)(1),
(2) Date: Aug. 3, 2018

(87) PCT Pub. No.: WO2017/134262
PCT Pub. Date: Aug. 10, 2017

(65) Prior Publication Data
US 2019/0046610 A1 Feb. 14, 2019

(30) Foreign Application Priority Data

Feb. 5, 2016 (EP) .................................. 16305137

(51) Int. Cl.
*A61K 38/00* (2006.01)
*A61K 38/17* (2006.01)
*A61P 31/18* (2006.01)

(52) U.S. Cl.
CPC ...... *A61K 38/1761* (2013.01); *A61K 38/1709* (2013.01); *A61P 31/18* (2018.01)

(58) Field of Classification Search
None
See application file for complete search history.

(56) References Cited

FOREIGN PATENT DOCUMENTS

WO 2015/121496 A1 8/2015

OTHER PUBLICATIONS

Mayank et al.; "Nucleoprotein of influenza A virus negatively impacts antiapoptotic protein AP15 to enhance E2F1-dependent apoptosis and virus replication"; Cell Death & Disease, vol. 6, Dec. 2015, pp. 1-11.
Rigou et al.; "The antiapoptotic protein AAC-11 interacts with and regulates Acinus-mediated DNA fragmentation"; The EMBO Journal, vol. 28, No. 11, Jun. 3, 2009, pp. 1576-1588.
Faye et al.; "Targeting AAC-11 in cancer therapy"; Expert Opinion on Therapeutic Targets, Informa Healthcare GB, vol. 14, No. 1, Jan. 1, 2010, pp. 57-65.

*Primary Examiner* — Thomas S Heard
(74) *Attorney, Agent, or Firm* — W&C IP

(57) ABSTRACT

The present invention relates to methods and pharmaceutical compositions for the treatment of viral infection.

3 Claims, 5 Drawing Sheets

Figure 1:
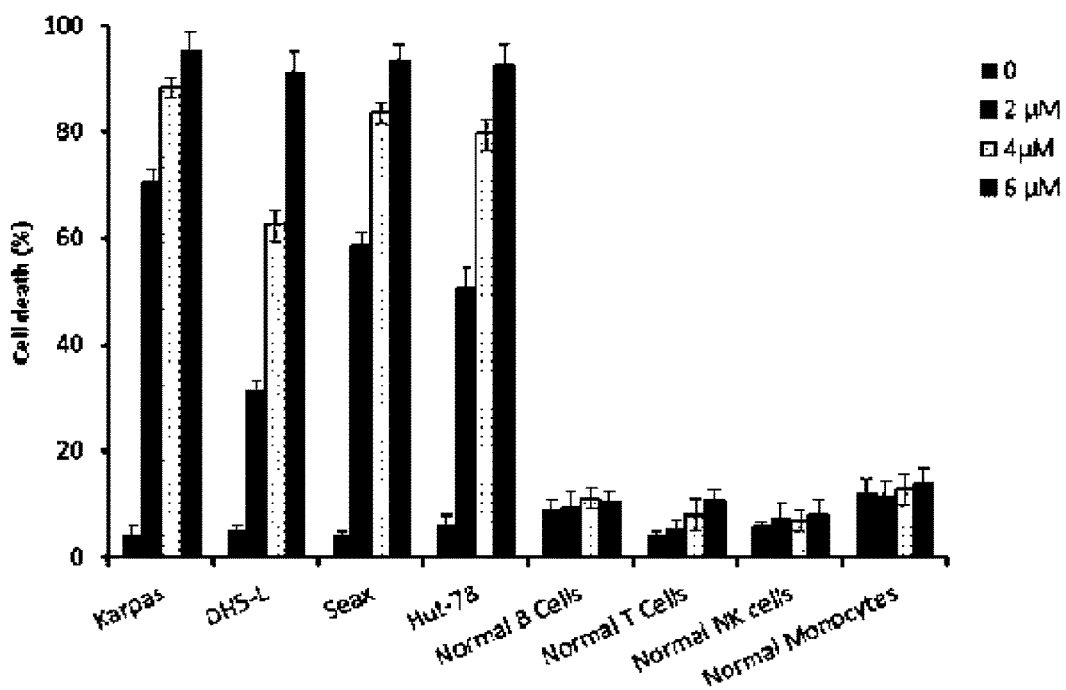

Specification includes a Sequence Listing.

Effect of various AAC11 derived peptides on infection of human primary CD4+ T cells with HIV-1 BaL

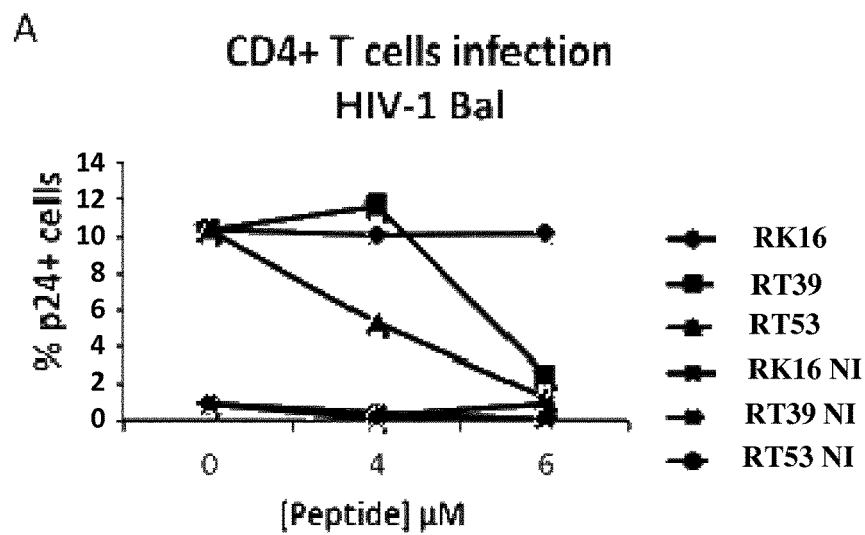
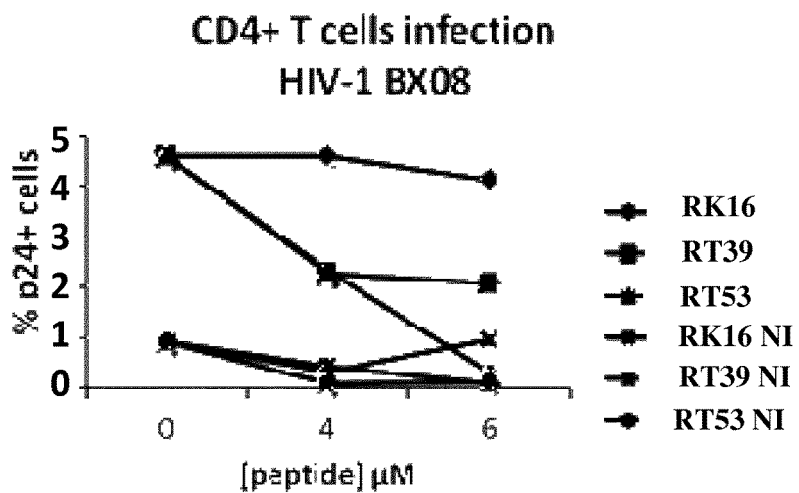
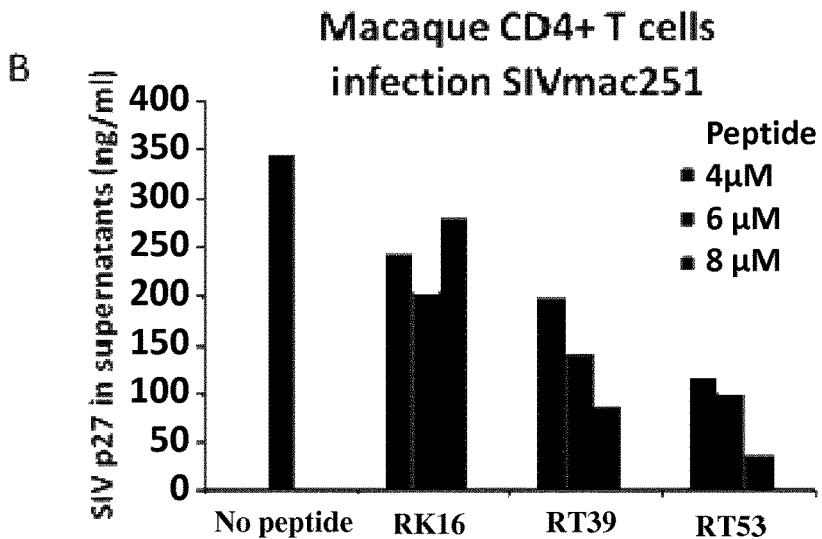
Figure 4 A and B 3 days post-infection with single cycle VSV-G pseudotyped GFP-reporter HIV-1
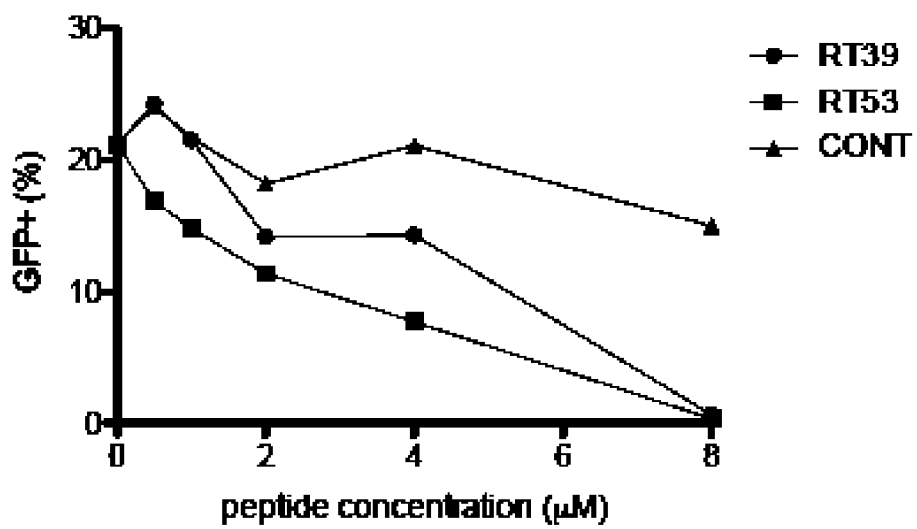
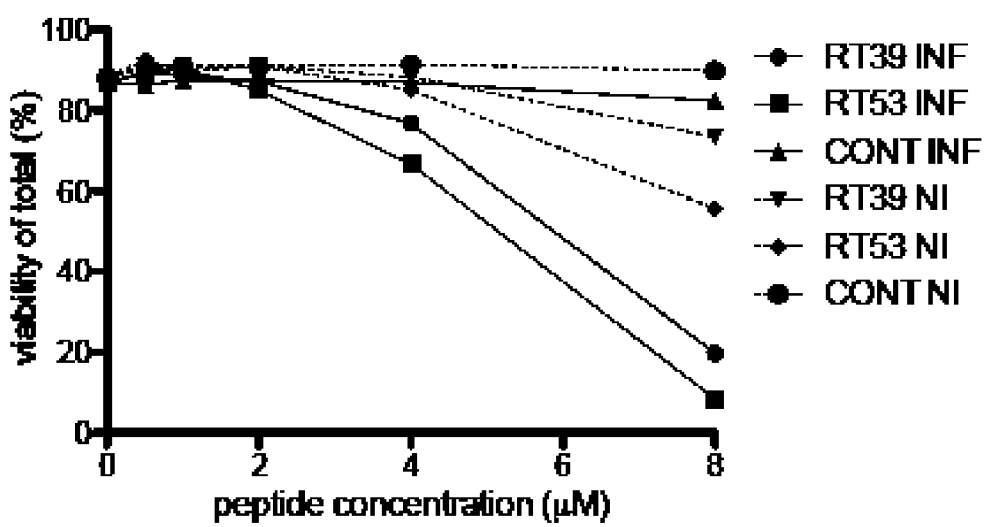
Figure 5

SEQUENCE LISTING

```
<160> NUMBER OF SEQ ID NOS: 8

<210> SEQ ID NO 1
<211> LENGTH: 524
<212> TYPE: PRT
<213> ORGANISM: Homo sapiens
```

```
<400> SEQUENCE: 1

Met Pro Thr Val Glu Glu Leu Tyr Arg Asn Tyr Gly Ile Leu Ala Asp
1               5                   10                  15

Ala Thr Glu Gln Val Gly Gln His Lys Asp Ala Tyr Gln Val Ile Leu
            20                  25                  30

Asp Gly Val Lys Gly Gly Thr Lys Glu Lys Arg Leu Ala Ala Gln Phe
        35                  40                  45

Ile Pro Lys Phe Phe Lys His Phe Pro Glu Leu Ala Asp Ser Ala Ile
    50                  55                  60

Asn Ala Gln Leu Asp Leu Cys Glu Asp Glu Val Ser Ile Arg Arg
65                  70                  75                  80

Gln Ala Ile Lys Glu Leu Pro Gln Phe Ala Thr Gly Glu Asn Leu Pro
                85                  90                  95

Arg Val Ala Asp Ile Leu Thr Gln Leu Leu Gln Thr Asp Ser Ala
                100                 105                 110

Glu Phe Asn Leu Val Asn Asn Ala Leu Leu Ser Ile Phe Lys Met Asp
            115                 120                 125

Ala Lys Gly Thr Leu Gly Gly Leu Phe Ser Gln Ile Leu Gln Gly Glu
130                 135                 140

Asp Ile Val Arg Glu Arg Ala Ile Lys Phe Leu Ser Thr Lys Leu Lys
145                 150                 155                 160

Thr Leu Pro Asp Glu Val Leu Thr Lys Glu Val Glu Glu Leu Ile Leu
                165                 170                 175

Thr Glu Ser Lys Lys Val Leu Glu Asp Val Thr Gly Glu Glu Phe Val
            180                 185                 190

Leu Phe Met Lys Ile Leu Ser Gly Leu Lys Ser Leu Gln Thr Val Ser
        195                 200                 205

Gly Arg Gln Gln Leu Val Glu Leu Val Ala Glu Gln Ala Asp Leu Glu
    210                 215                 220

Gln Thr Phe Asn Pro Ser Asp Pro Asp Cys Val Asp Arg Leu Leu Gln
225                 230                 235                 240

Cys Thr Arg Gln Ala Val Pro Leu Phe Ser Lys Asn Val His Ser Thr
                245                 250                 255

Arg Phe Val Thr Tyr Phe Cys Glu Gln Val Leu Pro Asn Leu Gly Thr
            260                 265                 270

Leu Thr Thr Pro Val Glu Gly Leu Asp Ile Gln Leu Glu Val Leu Lys
        275                 280                 285

Leu Leu Ala Glu Met Ser Ser Phe Cys Gly Asp Met Glu Lys Leu Glu
    290                 295                 300

Thr Asn Leu Arg Lys Leu Phe Asp Lys Leu Leu Glu Tyr Met Pro Leu
305                 310                 315                 320

Pro Pro Glu Glu Ala Glu Asn Gly Glu Asn Ala Gly Asn Glu Glu Pro
                325                 330                 335

Lys Leu Gln Phe Ser Tyr Val Glu Cys Leu Leu Tyr Ser Phe His Gln
            340                 345                 350

Leu Gly Arg Lys Leu Pro Asp Phe Leu Thr Ala Lys Leu Asn Ala Glu
        355                 360                 365

Lys Leu Lys Asp Phe Lys Ile Arg Leu Gln Tyr Phe Ala Arg Gly Leu
370                 375                 380

Gln Val Tyr Ile Arg Gln Leu Arg Leu Ala Leu Gln Gly Lys Thr Gly
385                 390                 395                 400

Glu Ala Leu Lys Thr Glu Asn Lys Ile Lys Val Val Ala Leu Lys
                405                 410                 415
```

```
Ile Thr Asn Asn Ile Asn Val Leu Ile Lys Asp Leu Phe His Ile Pro
                420                 425                 430

Pro Ser Tyr Lys Ser Thr Val Thr Leu Ser Trp Lys Pro Val Gln Lys
            435                 440                 445

Val Glu Ile Gly Gln Lys Arg Ala Ser Glu Asp Thr Thr Ser Gly Ser
450                 455                 460

Pro Pro Lys Lys Ser Ser Ala Gly Pro Lys Arg Asp Ala Arg Gln Ile
465                 470                 475                 480

Tyr Asn Pro Pro Ser Gly Lys Tyr Ser Ser Asn Leu Gly Asn Phe Asn
                485                 490                 495

Tyr Glu Gln Arg Gly Ala Phe Arg Gly Ser Arg Gly Arg Gly Arg Trp
            500                 505                 510

Gly Thr Arg Gly Asn Arg Ser Arg Gly Arg Leu Tyr
            515                 520

<210> SEQ ID NO 2
<211> LENGTH: 37
<212> TYPE: PRT
<213> ORGANISM: Artificial
<220> FEATURE:
<223> OTHER INFORMATION: Synthetic AAC-11-LZ (363-399)

<400> SEQUENCE: 2

Ala Lys Leu Asn Ala Glu Lys Leu Lys Asp Phe Lys Ile Arg Leu Gln
1               5                   10                  15

Tyr Phe Ala Arg Gly Leu Gln Val Tyr Ile Arg Gln Leu Arg Leu Ala
            20                  25                  30

Leu Gln Gly Lys Thr
        35

<210> SEQ ID NO 3
<211> LENGTH: 23
<212> TYPE: PRT
<213> ORGANISM: Artificial
<220> FEATURE:
<223> OTHER INFORMATION: Synthetic AAC-11-LZ (377-399)

<400> SEQUENCE: 3

Leu Gln Tyr Phe Ala Arg Gly Leu Gln Val Tyr Ile Arg Gln Leu Arg
1               5                   10                  15

Leu Ala Leu Gln Gly Lys Thr
            20

<210> SEQ ID NO 4
<211> LENGTH: 55
<212> TYPE: PRT
<213> ORGANISM: Artificial
<220> FEATURE:
<223> OTHER INFORMATION: Synthetic Antp-AAC-11-LZ (363-399) (RT53)

<400> SEQUENCE: 4

Arg Gln Ile Lys Ile Trp Phe Lys Lys Gln Asn Arg Arg Met Lys Trp
1               5                   10                  15

Lys Lys Ala Lys Leu Asn Ala Glu Lys Leu Lys Asp Phe Lys Ile Arg
            20                  25                  30

Leu Gln Tyr Phe Ala Arg Gly Leu Gln Val Tyr Ile Arg Gln Leu Arg
        35                  40                  45

Leu Ala Leu Gln Gly Lys Thr
50                  55
```

```
<210> SEQ ID NO 5
<211> LENGTH: 41
<212> TYPE: PRT
<213> ORGANISM: Artificial
<220> FEATURE:
<223> OTHER INFORMATION: Synthetic Antp-AAC-11-LZ (377-399) (RT39)

<400> SEQUENCE: 5

Arg Gln Ile Lys Ile Trp Phe Lys Lys Gln Asn Arg Arg Met Lys Trp
1               5                   10                  15

Lys Lys Leu Gln Tyr Phe Ala Arg Gly Leu Gln Val Tyr Ile Arg Gln
            20                  25                  30

Leu Arg Leu Ala Leu Gln Gly Lys Thr
        35                  40

<210> SEQ ID NO 6
<211> LENGTH: 31
<212> TYPE: PRT
<213> ORGANISM: Artificial
<220> FEATURE:
<223> OTHER INFORMATION: Synthetic Antp-AAC-11-LZ (379-391) (RL29)

<400> SEQUENCE: 6

Arg Gln Ile Lys Ile Trp Phe Lys Lys Gln Asn Arg Arg Met Lys Trp
1               5                   10                  15

Lys Lys Tyr Phe Ala Arg Gly Leu Gln Val Tyr Ile Arg Gln Leu
            20                  25                  30

<210> SEQ ID NO 7
<211> LENGTH: 18
<212> TYPE: PRT
<213> ORGANISM: Artificial
<220> FEATURE:
<223> OTHER INFORMATION: Synthetic Penetratin (Antp)

<400> SEQUENCE: 7

Arg Gln Ile Lys Ile Trp Phe Lys Lys Gln Asn Arg Arg Met Lys Trp
1               5                   10                  15

Lys Lys

<210> SEQ ID NO 8
<211> LENGTH: 11
<212> TYPE: PRT
<213> ORGANISM: Artificial
<220> FEATURE:
<223> OTHER INFORMATION: Synthetic Transactivator of Transcription cell
      penetrating sequence (TAT 47-57)

<400> SEQUENCE: 8

Tyr Gly Arg Lys Lys Arg Arg Gln Arg Arg Arg
1               5                   10
```

USE OF AAC-11 INHIBITORS FOR THE TREATMENT OF VIRAL INFECTION

FIELD OF THE INVENTION

The present invention relates to methods and pharmaceutical compositions for the treatment of viral infection.

BACKGROUND OF THE INVENTION

Viruses have evolved various strategies to exploit and manipulate host cell signaling pathways for their own purposes. In particular, viruses can modulate cellular apoptosis, which is largely antiviral in consequence, in order to increase their fitness and to complete their replication cycle. Even though some viruses promote apoptosis at the late stage of viral replication to facilitate viral release and spread, in some circumstances, virus-infected cells that do not undergo apoptosis are also known to play an important role in persistence as viral reservoirs. Consequently, restoring host cell apoptotic response against viral infection, and the destruction of the infected cell, constitutes an interesting antiviral strategy.

Viral infections are also known to induce multiple cellular stress responses and, as a result, viruses often modulate host stress responses, thought the upregulation of host cell stress-related genes, for their infection. Therefore, targeting of stress-response genes could lead to effective new antiviral therapies selectively aiming the infected cells.

There is a clear unmet medical need for safer, more effective drugs to combat viral infections, from HIV to the common cold. There is also a need for therapeutics effective against large spectrums of viruses, allowing their use in clinical settings where identifying pathogenic agents might be challenging. Consequently, the development of novel antiviral strategies combining reduced negative side effects with improved efficacy and which also have novel mechanisms of action are sought. In the case of HIV infection, the introduction of combination antiretroviral therapy (cART) has successfully reduced mortality and morbidity for infected patients who have access to the treatment. However, although cART is extremely efficient in controlling HIV replication it cannot eradicate the infection from the organism. HIV integrates its genetic information in the host cell genome, establishing viral reservoirs that escape immune surveillance and action of current therapies. As a consequence HIV replication readily resumes if treatment is interrupted and anti-HIV therapies have to be maintained for life. Long-term therapy can result in enhanced adverse effects that are complicated by overlapping toxicity profiles. Moreover, as they mostly target virus-coded products, antiviral drugs may encounter resistance problems due to the emergence of resistant viruses.

Accordingly, it is of the outmost priority to develop new therapeutic approaches and drugs that specifically target the infected cell rather than the viral replication and that will be suitable for effective and efficient treatment of viral infection and latent viral infection. In this way, it has been suggested that characterization of new therapeutic compounds in viral infection and latent viral infection may be highly desirable. One of the major difficulties to achieve such selective targeting is that there are not markers available allowing the identification of HIV-infected cells.

In this context, the inventors have discovered that the stress-related, anti-apoptotic protein AAC-11 is up-regulated upon HIV infection and contributes to cell survival of HIV infected cells. Inhibition of AAC-11 induce the specific cell death of infected cells or virus producing cells, including primary CD4+ T cells and macrophages, which are the main cell targets for HIV infection, and represent a novel therapeutic strategy to eradicate or control viral infections. Inhibition of AAC-11 may also induce specific cell death in sanctuaries sites as well as latently infected cells or cells producing low levels of virus.

There is no disclosure in the art of AAC-11 inhibitors effects in viral infection, the use of the AAC-11 inhibitors in the treatment of viral infection and the treatment of latent viral infection.

SUMMARY OF THE INVENTION

The present invention relates to methods and pharmaceutical compositions for the treatment of viral infection.

DETAILED DESCRIPTION OF THE INVENTION

The inventors investigated the role of AAC-11 in viral infection and demonstrated that the stress-related, anti-apoptotic protein AAC-11 is up-regulated upon HIV infection in HIV-1 infected CD4+ T cells and contributes to cell survival of HIV infected cells a higher expression of AAC-11. The inventors also demonstrated that AAC-11 inhibition using AAC-11 derived peptides induce the selective elimination of HIV infected CD4+ T cells. The inventors also demonstrated that AAC-11 derived peptides administered before or after HIV infection block HIV-1 infection in human macrophages. Therefore, inhibition of AAC-11 results in the specific cell death of infected cells or virus producing cells, including cells typically found in sanctuaries sites.

Accordingly, the present invention relates to an AAC-11 inhibitor compound for use in the treatment of viral infection in a subject in need thereof.

As used herein, the term "subject" denotes a mammal. Typically, a subject according to the invention refers to any subject (preferably human) afflicted with or susceptible to be afflicted with viral infection. In a particular embodiment, the term "subject" refers to subject afflicted with or susceptible to be afflicted with latent viral infection.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "viral infection" has its general meaning in the art and refers to viral diseases such as revised in the World Health Organisation Classification (ICD-10) A08, A80-B34 and B97. The term "viral infection" also refers to viral diseases such as revised in the National Library of Medicine MeSH (D014777): arbovirus infections, viral bronchiolitis, viral central nervous system diseases, DNA virus infections, viral encephalitis, viral eye infections, chronic fatigue syndrome, viral hepatitis, viral meningitis, opportunistic infections, viral pneumonia, RNA virus infections, sexually viral transmitted diseases, viral skin diseases, slow virus diseases, tumor virus infections, viremia, zoonoses, hepatitis C virus (HCV infection), human immunodeficiency virus infection (HIV infection), Ebola virus infection, influenza virus infection, and herpes virus infection. The term "viral infection" also refers to latent viral infection.

As used herein the term "AAC-11" has its general meaning in the art and refers to the antiapoptosis clone 11 protein that is also known as apoptosis inhibitor 5 (Api5) or FIF. An exemplary human polypeptide sequence of AAC-11 is deposited in the GenBank database accession number: Q9BZZ5 set forth as SEQ ID NO:1.

```
SEQ ID NO: 1 for AAC-11 Q9BZZ5
MPTVEELYRNYGILADATEQVGQHKDAYQVILDGVKGGTKEKRLAAQFIP

KFFKHFPELADSAINAQLDLCEDEDVSIRRQAIKELPQFATGENLPRVAD

ILTQLLQTDDSAEFNLVNNALLSIFKMDAKGTLGGLFSQILQGEDIVRER

AIKFLSTKLKTLPDEVLTKEVEELILTESKKVLEDVTGEEFVLFMKILSG

LKSLQTVSGRQQLVELVAEQADLEQTFNPSDPDCVDRLLQCTRQAVPLFS

KNVHSTRFVTYFCEQVLPNLGTLTTPVEGLDIQLEVLKLLAEMSSFCGDM

EKLETNLRKLFDKLLEYMPLPPEEAENGENAGNEEPKLQFSYVECLLYSF

HQLGRKLPDFLTAKLNAEKLKDFKIRLQYFARGLQVYIRQLRLALQGKTG

EALKTEENKIKVVALKITNNINVLIKDLFHIPPSYKSTVTLSWKPVQKVE

IGQKRASEDTTSGSPPKKSSAGPKRDARQIYNPPSGKYSSNLGNFNYEQR

GAFRGSRGGRGWGTRGNRSRGRLY
```

The term "AAC-11 inhibitor" has its general meaning in the art and refers to a compound that selectively blocks or inactivates the AAC-11. The term "AAC-11 inhibitor" also refers to a compound that selectively blocks the binding of AAC-11 to its interacting protein partners and downstream effectors. The term "AAC-11 inhibitor" also refers to a compound able to prevent the action of AAC-11, for example by inhibiting the AAC-11 controls of downstream effectors. As used herein, the term "selectively blocks or inactivates" refers to a compound that preferentially binds to and blocks or inactivates AAC-11 with a greater affinity and potency, respectively, than its interaction with the other sub-types of the leucine zipper family. The term "AAC-11 inhibitor" also relates to a compound that selectively blocks the interaction and the binding of the AAC-11 leucin zipper domain to its interacting protein partners. The term "AAC-11 inhibitor" also refers to a compound able to bind to AAC-11 interacting protein partners or a portion of AAC-11 interacting protein partners. The term "AAC-11 inhibitor" also refers to a compound that inhibits AAC-11 expression or induces AAC-11 degradation. Typically, an AAC-11 inhibitor compound is a small organic molecule, a polypeptide, an aptamer, an intra-antibody, an oligonucleotide or a ribozyme.

Tests and assays for determining whether a compound is an AAC-11 inhibitor are well known by the skilled person in the art such as described in Faye and Poyet, 2010; Rigou et al., 2009; and WO2015121496.

AAC-11 inhibitors are well-known in the art as illustrated by Faye and Poyet, 2010; Rigou et al., 2009; and WO2015121496.

In one embodiment of the invention, AAC-11 inhibitor compounds include but are not limited to isolated, synthetic or recombinant AAC-11 derived peptides ("AAC-11-derived peptides").

In one embodiment, AAC-11 inhibitor compounds include but are not limited to isolated, synthetic or recombinant AAC-11 leucine-zipper (LZ) derived peptides ("AAC-11-LZ-derived peptides") such as described in WO2015121496.

Accordingly, the present invention also relates to a polypeptide comprising or consisting of
i) an amino acid sequence ranging from the phenylalanine residue at position 380 to the leucine residue at position 384 in SEQ ID NO:1 or,
ii) an amino acid sequence having at least 70% of identity with the amino acid sequence ranging from the phenylalanine residue at position 380 to the leucine residue at position 384 in SEQ ID NO:1, or
iii) an amino acid sequence which is a retro-inverso of the amino acid sequence ranging from the phenylalanine residue at position 380 to the leucine residue at position 384 in SEQ ID NO:1 or,
iv) an amino acid sequence which is retro-inverso of the amino acid sequence having at least 70% of identity with the amino acid sequence ranging from the phenylalanine residue at position 380 to the leucine residue at position 384 in SEQ ID NO:1, for use in the treatment of viral infection in a subject in need thereof.

In a particular embodiment, the present invention relates to a polypeptide comprising or consisting of
i) an amino acid sequence ranging from the leucine residue at position 377 to the threonine residue at position 399 in SEQ ID NO:1 or,
ii) an amino acid sequence having at least 70% of identity with the amino acid sequence ranging from the leucine residue at position 377 to the threonine residue at position 399 in SEQ ID NO:1, or
iii) an amino acid sequence which is a retro-inverso of the amino acid sequence ranging from the leucine residue at position 377 to the threonine residue at position 399 in SEQ ID NO:1 or,
iv) an amino acid sequence which is retro-inverso having at least 70% of identity with the amino acid sequence ranging from the leucine residue at position 377 to the threonine residue at position 399 in SEQ ID NO:1, for use in the treatment of viral infection in a subject in need thereof.

In a particular embodiment, the present invention relates to a polypeptide comprising or consisting of i) an amino acid sequence ranging from the alanine residue at position 363 to the threonine residue at position 399 in SEQ ID NO:1 or, ii) an amino acid sequence having at least 70% of identity with the amino acid sequence ranging from the alanine residue at position 363 to the threonine residue at position 399 in SEQ ID NO:1, or iii) an amino acid sequence which is a retro-inverso of the amino acid sequence ranging from the alanine residue at position 363 to the threonine residue at position 399 in SEQ ID NO:1 or, iv) an amino acid sequence which is retro-inverso having at least 70% of identity with the amino acid sequence ranging from the alanine residue at position 363 to the threonine residue at position 399 in SEQ ID NO:1, for use in the treatment of viral infection in a subject in need thereof.

In some embodiment, the present invention relates to the polypeptide comprising or consisting of i) an amino acid sequence ranging from the lysine residue at position 371 to the leucine residue at position 391 in SEQ ID NO:1 or, ii) an amino acid sequence having at least 70% of identity with the amino acid sequence ranging from the lysine residue at position 371 to the leucine residue at position 391 in SEQ ID NO:1, or iii) an amino acid sequence which is a retro-inverso of the amino acid sequence ranging from the lysine residue at position 371 to the leucine residue at position 391 in SEQ ID NO:1 or, iv) an amino acid sequence which is retro-inverso having at least 70% of identity with the amino acid sequence ranging from the lysine residue at position 371 to the leucine residue at position 391 in SEQ ID NO:1, for use in the treatment of viral infection in a subject in need thereof.

In some embodiment, the present invention relates to the polypeptide comprising or consisting of i) an amino acid sequence ranging from the lysine residue at position 371 to the threonine residue at position 399 in SEQ ID NO:1 or, ii) an amino acid sequence having at least 70% of identity with the amino acid sequence ranging from the lysine residue at position 371 to the threonine residue at position 399 in SEQ ID NO:1, or iii) an amino acid sequence which is a retro-inverso of the amino acid sequence ranging from the lysine residue at position 371 to the threonine residue at position 399 in SEQ ID NO:1 or, iv) an amino acid sequence which is retro-inverso having at least 70% of identity with the amino acid sequence ranging from the lysine residue at position 371 to the threonine residue at position 399 in SEQ ID NO:1, for use in the treatment of viral infection in a subject in need thereof.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence. Amino acid sequence identity is preferably determined using a suitable sequence alignment algorithm and default parameters, such as BLAST P (Karlin and Altschul, 1990).

The term "retro-inverso amino acid sequence" relates to an isomeric form of an amino acid sequence in which the direction of the amino acid sequence is reversed and the chirality of each amino acid residue is inverted. Retro-inverso amino acid sequence of the present invention may be composed by D-amino acids assembled in the reverse order from that of the parental amino acid sequence-sequence.

In some embodiments, the polypeptide of the invention comprises 4, 5, 6, 7, 8, 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100 amino acids. In some embodiments, the polypeptide of the invention comprises less than 50 amino acids. In some embodiments, the polypeptide of the invention comprises less than 30 amino acids. In some embodiments, the polypeptide of the invention comprises less than 25 amino acids. In some embodiments, the polypeptide of the invention comprises less than 20 amino acids. In some embodiments, the polypeptide of the invention comprises less than 15 amino acids.

In another embodiment, AAC-11 inhibitor compound of the invention is a fusion protein comprising the polypeptide according to the invention that is fused to at least one heterologous polypeptide.

The term "fusion protein" refers to the polypeptide according to the invention that is fused directly or via a spacer to at least one heterologous polypeptide.

According to the invention, the fusion protein comprises the polypeptide according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the polypeptide is fused to the (first or last) amino acid at the terminal end (N or C-terminal end) of the heterologous polypeptide.

In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide.

As used herein, the term "spacer" refers to a sequence of at least one amino acid that links the polypeptide of the invention to the heterologous polypeptide. Such a spacer may be useful to prevent steric hindrances.

In some embodiments, the heterologous polypeptide is a cell-penetrating peptide, a Transactivator of Transcription (TAT) cell penetrating sequence, a cell permeable peptide or a membranous penetrating sequence.

The term "cell-penetrating peptides" are well known in the art and refers to cell permeable sequence or membranous penetrating sequence such as penetratin, TAT mitochondrial penetrating sequence, octa-arginine (R8) and compounds described in Bechara and Sagan, 2013; Jones and Sayers, 2012; Khafagy el and Morishita, 2012; Malhi and Murthy, 2012.

In a particular embodiment, the heterologous polypeptide is an internalization sequence derived either from the homeodomain of Drosophila Antennapedia/Penetratin (Antp) protein (amino acids 43-58; SEQ ID NO: 6) or the Transactivator of Transcription (TAT) cell penetrating sequences (SEQ ID NO: 7).

In a particular embodiment, one, two or three glycine residue are added at the C-terminal end of the TAT cell penetrating sequences (SEQ ID NO: 7).

In some embodiments, the fusion protein of the present invention comprises or consists of a sequence selected from the group consisting of SEQ ID NO: 4, and SEQ ID NO: 5.

In another embodiment, the heterologous polypeptide is a viral infection therapeutic polypeptide.

The term "viral infection therapeutic polypeptide" refers to any polypeptide that has anti-viral infection activities (e.g., viral replication inhibition, infected cell proliferation or survival, immune response modulation, viral adhesion and entry into host cell). Several such polypeptides are known in the art. (See. e.g., U.S. Pat. Nos. 5,382,657; 5,981,709; and 5,951,974; Zhang and Lu, 2015; Skalickova et al., 2015; Lazear et al., 2015).

In some embodiment, the heterologous polypeptide is a viral infected cell targeting agent.

Viral infected cell targeting agents include but are not limited to antibodies directed against viral epitopes, antibodies or agents binding viral infected cell and Host-targeting agents such described in Zeisel et al., 2013 and Ramana et al., 2014.

The polypeptides or fusion proteins of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides or fusion proteins, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides or fusion proteins of the invention can be synthesized by recombinant DNA techniques as is now well-known in the art. For example, these fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

Polypeptides or fusion proteins of the invention can be used in an isolated (e.g., purified) form or contained in a vector, such as a membrane, lipid vesicle (e.g. a liposome), erythrocyte or nanoparticle.

In specific embodiments, it is contemplated that polypeptides or fusion proteins according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

For example, Pegylation is a well-established and validated approach for the modification of a range of polypeptides (Chapman, 2002). The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein (Cunningham-Rundles et. al., 1992); and (e) improved thermal and mechanical stability of the PEGylated polypeptide.

Therefore, advantageously, the polypeptides of the invention may be covalently linked with one or more polyethylene glycol (PEG) group(s). One skilled in the art can select a suitable molecular mass for PEG, based on how the pegylated polypeptide will be used therapeutically by considering different factors including desired dosage, circulation time, resistance to proteolysis, immunogenicity, etc.

In one embodiment, the PEG of the invention terminates on one end with hydroxy or methoxy, i.e., X is H or $CH_3$ ("methoxy PEG"). In addition, such a PEG can consist of one or more PEG side-chains which are linked together. PEGs with more than one PEG chain are called branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. One form of PEGs includes two PEG side-chains (PEG2) linked via the primary amino groups of a lysine (Monfardini et al., 1995).

To effect covalent attachment of PEG groups to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPDX-PEG, NCO-PEG, NPC-PEG, CDI-PEG, ALD-PEG, TRES-PEG, VS-PEG, IODO-PEG, and MAL-PEG, and branched PEGs such as PEG2-NHS.

The conjugation of the polypeptides or fusion proteins and the activated polymer molecules is conducted by use of any conventional method. Conventional methods are known to the skilled artisan. The skilled person will be aware that the activation method and/or conjugation chemistry to be used depends on the attachment group(s) of the polypeptides as well as the functional groups of the PEG molecule (e.g., being amine, hydroxyl, carboxyl, aldehyde, ketone, sulfhydryl, succinimidyl, maleimide, vinylsulfone or haloacetate).

In one embodiment, polypeptides are conjugated with PEGs at amino acid D and E (for COOH), T, Y and S (for OH), K (for $NH_2$), C (for SH if at least one cysteine is conserved) or/and Q and N (for the amide function).

In one embodiment, additional sites for PEGylation can be introduced by site-directed mutagenesis by introducing one or more lysine residues. For instance, one or more arginine residues may be mutated to a lysine residue. In another embodiment, additional PEGylation sites are chemically introduced by modifying amino acids on polypeptides of the invention.

In one embodiment, PEGs are conjugated to the polypeptides or fusion proteins through a linker. Suitable linkers are well known to the skilled person. A preferred example is cyanuric chloride ((Abuchowski et al., 1977); U.S. Pat. No. 4,179,337).

Conventional separation and purification techniques known in the art can be used to purify pegylated polypeptides of the invention, such as size exclusion (e.g. gel filtration) and ion exchange chromatography. Products may also be separated using SDS-PAGE.

In one embodiment, the pegylated polypeptides provided by the invention have a serum half-life in vivo at least 50%, 75%, 100%, 150% or 200% greater than that of an unmodified polypeptide.

In another embodiment, the AAC-11 inhibitor compound of the invention is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996). Then after raising aptamers directed against AAC-11 of the invention as above described, the skilled man in the art can easily select those blocking or inactivating AAC-11.

In one embodiment, the AAC-11 inhibitor compound of the invention is an AAC-11 expression inhibitor.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs, which are modified, by processes such as capping, polyadenylation, methylation, and editing, and proteins (e.g., AAC-11) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit the expression of a gene.

AAC-11 expression inhibitors for use in the present invention may be based on antisense oligonucleotide constructs. Anti-sense oligonucleotides, including anti-sense RNA molecules and anti-sense DNA molecules, would act to directly block the translation of AAC-11 mRNA by binding thereto and thus preventing protein translation or increasing mRNA degradation, thus decreasing the level of AAC-11 proteins, and thus activity, in a cell. For example, antisense oligonucleotides of at least about 15 bases and complementary to unique regions of the mRNA transcript sequence encoding AAC-11 can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as AAC-11 expression inhibitors for use in the present invention. AAC-11 gene expression can be reduced by contacting the subject or cell with a small double stranded RNA (dsRNA), or a vector or construct causing the production of a small double stranded RNA, such that AAC-11 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as AAC-11 expression inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of AAC-11 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as AAC-11 expression inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone. Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing AAC-11. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which nonessential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W. H. Freeman C. O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Typically the AAC-11 inhibitor compounds according to the invention as described above are administered to the subject in a therapeutically effective amount.

By a "therapeutically effective amount" of the inhibitor of the present invention as above described is meant a sufficient amount of the inhibitor for treating viral infection at a reasonable benefit/risk ratio applicable to any medical treatment. It will be understood, however, that the total daily usage of the inhibitors and compositions of the present invention will be decided by the attending physician within the scope of sound medical judgment. The specific therapeutically effective dose level for any particular subject will depend upon a variety of factors including the disorder being treated and the severity of the disorder; activity of the specific inhibitor employed; the specific composition employed, the age, body weight, general health, sex and diet of the subject; the time of administration, route of administration, and rate of excretion of the specific inhibitor employed; the duration of the treatment; drugs used in combination or coincidential with the specific inhibitor employed; and like factors well known in the medical arts. For example, it is well within the skill of the art to start doses of the inhibitor at levels lower than those required to achieve the desired therapeutic effect and to gradually increase the dosage until the desired effect is achieved. However, the daily dosage of the products may be varied over a wide range from 0.0001 to 1,000 mg per adult per day. Typically, the compositions contain 0.0001, 0.0005, 0.001, 0.005, 0.01, 0.05, 0.1, 0.5, 1.0, 2.5, 5.0, 10.0, 15.0, 25.0, 50.0, 100, 250 and 500 mg of the inhibitor of the present invention for the symptomatic adjustment of the dosage to the subject to be treated. A medicament typically contains from about 0.01 mg to about 500 mg of the inhibitor of the present invention, preferably from 1 mg to about 100 mg of the inhibitor of the present invention. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the inhibitor according to the invention may be used in a concentration between 0.01 µM and 20 µM, particularly, the inhibitor of the invention may be used in a concentration of 0.01, 0.05, 0.1, 0.5, 1.0, 2.5, 5.0, 10.0, 15.0, 20.0 µM.

In a further aspect, the present invention relates to the inhibitor according to the invention in combination with one or more anti-viral infection compound for use in treating viral infection in a subject in need thereof.

The term "anti-viral infection compound" has its general meaning in the art and refers to compounds used in the treatment of viral infection such as interferon-alpha (IFN-alpha), PEGylated IFN-alpha (PEG-IFN), ribavirin, MX-3253, viral replication inhibitors such as Miravirsen/SPC3649, Statins, SCY-635, Alisporivir/Debio 025; and viral entry inhibitors such as anti-CD81 mAbs, anti-SR-BI mAbs, ITX 5061, Erlotinib, Ezetimibe (Lazear et al., 2015. The term "anti-viral infection compound" also refers to HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100; HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MW-150, and TMC-120, TMC-278 (rilpivirine), BILR 355 BS, VRX 840773, UK-453,061, RDEA806; HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine; HIV nucleotide inhibitor of reverse transcriptase, e.g., tenofovir, tenofovir disoproxil fumarate+emtricitabine, tenofovir disoproxil fumarate+emtricitabine+efavirenz, tenefovir alafenamide fumarate and adefovir; HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), dolutegravir, S/GSK1265744 (cabotegravir), BMS-707035, MK-2048, BA-011, BMS-538158, GSK364735C; gp41 inhibitor, e.g., enfuvirtide, sifuvirtide, FB006M, TRI-1144, SPC3, DES6, Locus gp41, CovX, and REP 9; CXCR4 inhibitor, e.g., AMD-070; entry inhibitor, e.g., SPO1A, TNX-355; gp120 inhibitor, e.g., BMS-488043 and BlockAide/CR; G6PD and NADH-oxidase inhibitor, e.g., immunitin; CCR5 inhibitor, e.g., aplaviroc, vicriviroc, INCB9471, PRO-140, INCB15050, PF-232798, CCR5 mAb004, and maraviroc; interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albufcron; ribavirin analogs, e.g., rebetol, copegus, levovirin, VX-497, and viramidine (taribavirin); NS5a inhibitors, e.g., A-831 and A-689; NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; non-nucleoside inhibitors of HCV, e.g., benzimidazole derivatives, benzo-1,2,4-thiadiazine derivatives, and phenylalanine derivatives; other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, G1-5005, ANA-975 (isatoribine), XTL-6865, ANA 971, NOV-205, tarvacin, EHC-18, and NIM811; pharmacokinetic enhancers, e.g., BAS-100 and SPI452, 20)RNAse H inhibitors, e.g., ODN-93 and ODN-112; other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

According to the present invention, the inhibitor of the invention is administered sequentially or concomitantly with one or more anti-viral infection compound.

The present invention also relates to a method for treating viral infection in a subject in need thereof, comprising the step of administering to said subject the AAC-11 inhibitor compound of the invention.

In a further aspect, the present invention relates to a method of screening a candidate compound for use as a drug for treating viral infection in a subject in need thereof, wherein the method comprises the steps of:
  providing an AAC-11, providing a cell, tissue sample or organism expressing a AAC-11,
  providing a candidate compound such as a small organic molecule, a polypeptide, an aptamer, or an intra-antibody,
  measuring the AAC-11 activity,
  and selecting positively candidate compounds that inhibit AAC-11 activity.

Methods for measuring AAC-11 activity are well known in the art (Faye and Poyet, 2010; Rigou et al., 2009; and WO2015121496). For example, measuring the AAC-11 activity involves determining a Ki on the AAC-11 cloned and transfected in a stable manner into a CHO cell line, CD4+ T cells and macrophages, measuring viral infection and measuring apoptosis and cell viability in the present or absence of the candidate compound.

Tests and assays for screening and determining whether a candidate compound is an AAC-11 inhibitor are well known in the art (Faye and Poyet, 2010; Rigou et al., 2009; and WO2015121496). In vitro and in vivo assays may be used to assess the potency and selectivity of the candidate compounds to inhibit AAC-11 activity.

Activities of the candidate compounds, their ability to bind AAC-11 and their ability to inhibit AAC-11 activity may be tested using isolated CHO cell line cloned and transfected in a stable manner by the human AAC-11.

Activities of the candidate compounds and their ability to bind to the AAC-11 may be assessed by the determination of a Ki on the AAC-11 cloned and transfected in a stable manner into a CHO cell line, CD4+ T cells and macrophages, measuring viral infection and measuring apoptosis and cell viability in the present or absence of the candidate compound such as described in the example. The ability of the candidate compounds to inhibit AAC-11 activity may be assessed by fluorescence resonance energy transfer (FRET Assay) such as described in the example.

The candidate compounds may be screened in a functional assay such as FRET-based protocol. Recombinant proteins consisting of AAC-11 fused to the N-terminus of cyan fluorescent protein (AAC-11-CFP) and a portion of Acinus, containing amino acids 840 to 918 (hereafter named ASID), fused to the N-terminus of yellow fluorescent protein (ASID-YFP) will be allowed to interact at 37° C. for 1 h (at 85 nM monomer concentration). The candidate compounds are added to a final concentration of 25 µM and the mixtures incubated for 1 h at 25° C. After excitation of CFP at 433 nm, both the CFP fluorescence at 475 nm and the YFP fluorescence at 525 nm are measured in a 96-well fluorescent plate reader. AAC-11-ASID complex formation permits FRET from CFP to YFP, thus enhancing the emission of YFP at 525 nm. Compounds that dissociate AAC-11-CFP/ASID-YFP complexes will then increase the emission of CFP and decrease the emission of YFP, resulting in lower ratio intensities [525 nm/475 nm]. Candidate inhibitors of AAC-11-ASID interaction identified by FRET are further investigated by an ELISA assay, where AAC-11 is immobilized on an ELISA plate, following incubation with ASID-GFP together with the candidate compounds. The inhibition of AAC-11-ASID binding is determined colorimetrically by using a horseradish peroxidase-conjugated GFP antibody. The biological effect of the top inhibitors is then evaluated.

The inhibitors of the invention may be used or prepared in a pharmaceutical composition.

In one embodiment, the invention relates to a pharmaceutical composition comprising the inhibitor of the invention and a pharmaceutical acceptable carrier for use in treating viral infection in a subject of need thereof.

Typically, the inhibitor of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, intramuscular, intravenous, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, intraperitoneal, intramuscular, intravenous and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active inhibitors in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further compound which is used in the treatment of viral infection.

In one embodiment, said additional active compounds may be contained in the same composition or administrated separately.

In another embodiment, the pharmaceutical composition of the invention relates to combined preparation for simultaneous, separate or sequential use in treating viral infection in a subject in need thereof.

The invention also provides kits comprising the inhibitor of the invention. Kits containing the inhibitor of the invention find use in therapeutic methods.

The invention will be further illustrated by the following figures and examples. However, these examples and figures should not be interpreted in any way as limiting the scope of the present invention.

FIGURES

FIG. 1: Antp-AAC-11-LZ (377-399) peptide induced cancer cells, but not normal cells, death under condition of low-serum stress. The indicated cell lines or blood cells from healthy donors were treated for 24 hours in a 37° C. incubator (5% $CO_2$) with increasing concentrations of the Antp-AAC-11-LZ (377-399) before Annexin-V and PI staining. The percentages refer to Annexin-V-positive or Annexin-V-positive/PI-positive staining.

Figure 2:
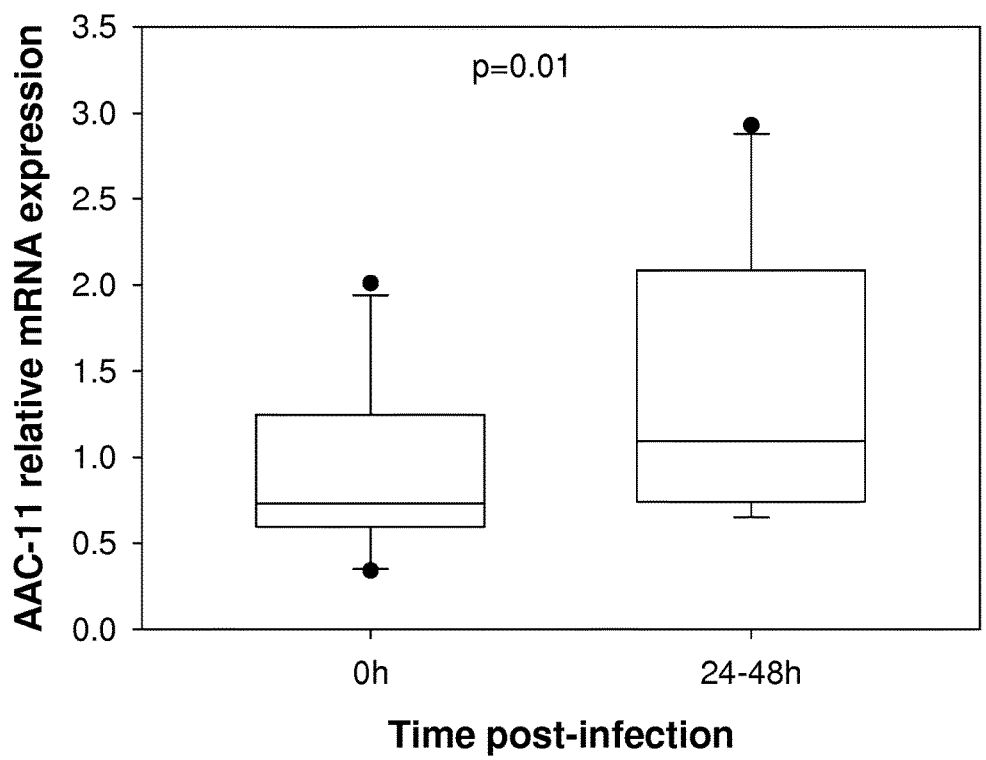

FIG. 2: Higher expression of AAC-11 in HIV-1 infected CD4+ T cells. Relative mRNA expression of AAC-11 in PHA-activated CD4+ T cells from 10 healthy donors at the time of infection and after 24 or 48 h post-infection with VSV-G-pseudotyped HIV-1 particles carrying the GFP reporter gene. Box plots represent median and 25-75% ranges. Whiskers represent 10 and 90% values. Outliers are shown. Differences between non-infected and infected cells were calculated with a Wilcoxon signed rank test (Sigmaplot, Systat Software).

Figure 3:
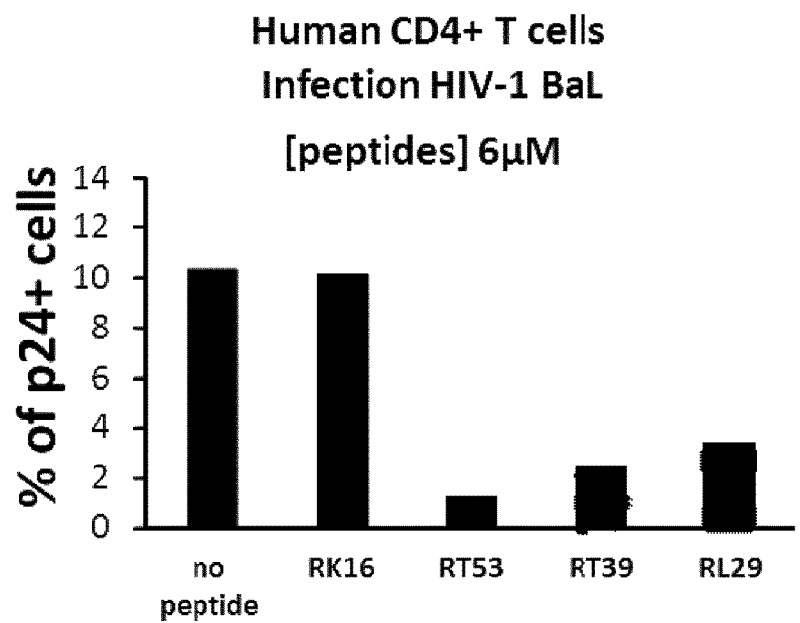

FIG. 3: AAC-11 derived peptides induce the selective elimination of HIV infected CD4+ T cells. CD4+ T cells were infected with HIV-1 BaL in the presence of 6 µM of the AAC-11 derived peptides RL29, RT39, RT53 or a control (penetratin, RK16) peptide. Three days later HIV-1 replication was monitored by measuring p24 antigen in supernatants.

FIG. 4: AAC-11 derived peptides induce the selective elimination of HIV infected human CD4+ T cells and SIVmac infected macaque CD4+ T cells. (A) Human CD4+ T cells were infected (or not, NI) with the laboratory adapted HIV-1BaL (upper panel) or the primary strain HIV-1BX08 (bottom panel) in the presence of increasing amounts of the AAC-11 derived peptides RT39, RT53 or a control peptide (penetratin, RK16). Three days later HIV-1 replication was monitored by measuring p24 antigen in supernatants. (B) Macaque CD4+ T cells were infected with SIVmac251 in the absence or presence of increasing amounts of the AAC-11 derived peptides RT39, RT53 or a control peptide (penetratin, RK16). Three days later SIVmac251replication was monitored by measuring p27 antigen in supernatants.

FIG. 5: AAC-11 derived peptides induce the selective elimination of HIV infected CD4+ T cells. CD4+ T cells were infected (or not, NI) with VSV-G HIV-1-particles in the presence of increasing amounts of the AAC-11 derived peptides RT39, RT53 or a control (penetratin, Cont) peptide. Three days later the percentage of infected and death cells were analyzed by flow cytometry. A. Percentage of GFP+ cells after infection and three days in culture in the absence or in presence of increasing concentration of peptides. B. Percentage of viable cells after infection or not and three days in culture in the presence of increasing amounts of peptides.

Figure 6:
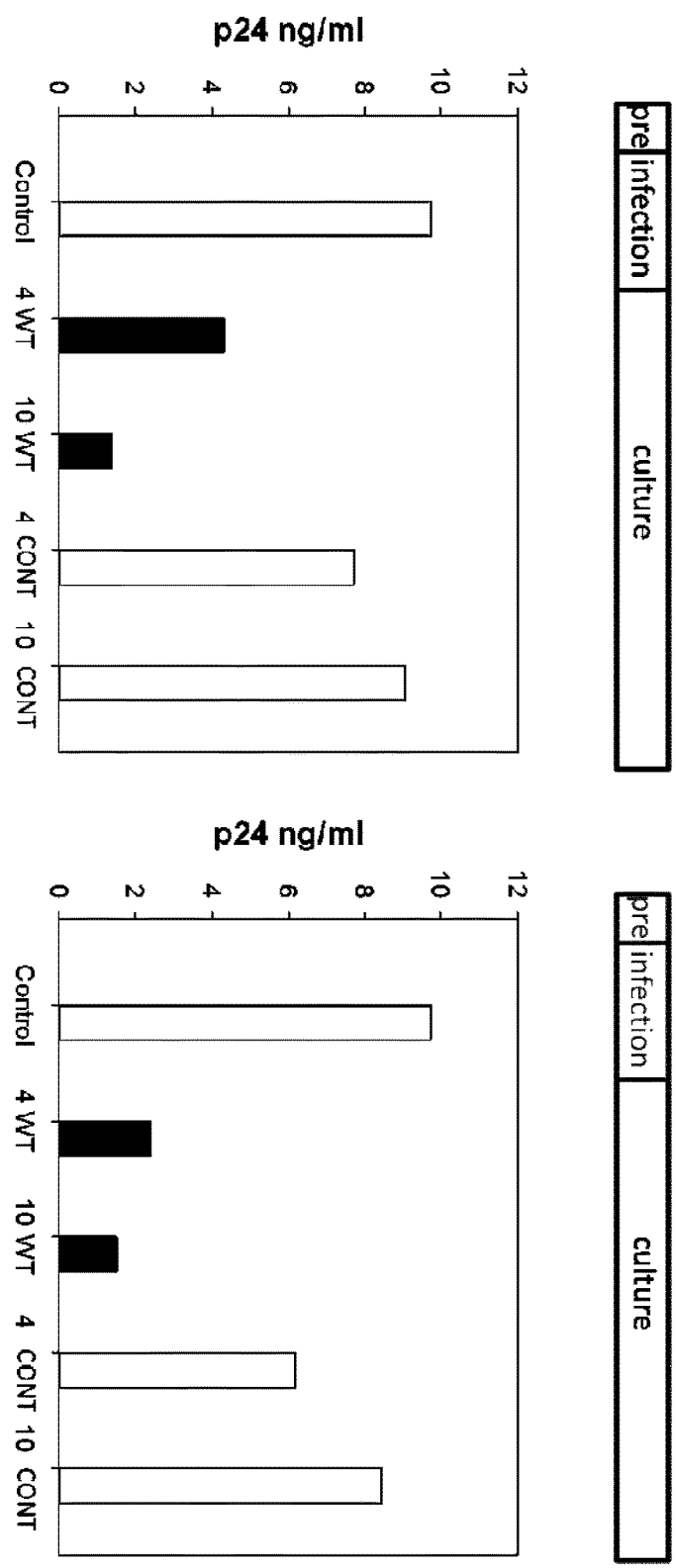

FIG. 6: AAC-11 derived peptides block HIV-1 infection in human macrophages. MDM were infected with productive HIV-1 BaL and culture for three days in the absence of peptides or in the presence of 4 or 8 µM of the RT53 (WT) and the control (Cont) peptides. The peptides were added to the culture 10 minutes before infection, kept during spinoculation and washed after two hours (left) or added two hours after infection and kept in the culture for the three days (right).

EXAMPLE

Material & Methods

Peptides Design and Synthesis

The inventors have designed peptides that encompass the leucine-zipper (LZ) domain of AAC-11 (residues 363-399). Furthermore, we have designed peptides that have the leucine residues (position 377, 384 and 391, AAC-11 numbering) mutated to glycine to determine if this will still be effective against viral infection. Peptides (>95% pure) were synthesized by Proteogenics Strasbourg-France. Peptides used here were modified by N-terminal acetylation and C-terminal amidation. Peptides were diluted at a concentration of 1 mM in H2O and kept frozen at −70° C. The peptide RT53 corresponds to residues 363 to 399 of AAC-11 fused at the N-terminus with the penetratin sequence. The peptide RT39 corresponds to residues 377 to 399 of AAC-11 fused at the N-terminus with the penetratin sequence. The peptide RL29 corresponds to residues 379 to 391 of AAC-11 fused at the N-terminus with the penetratin sequence. The sequences of used peptides are listed below.

Cell Isolation

Peripheral blood mononuclear cells (PBMC) were freshly isolated from blood samples from healthy blood donors from the Etablissement français du sang (EFS) in the context of the collaboration agreement between the EFS and Institut Pasteur or from non-experimentally infected cynomolgus macaques (*Macaca fascicularis*). CD4+ and CD14+ cells were purified (>95%) from PBMCs by positive selection with antibody-coated magnetic beads in a Robosep instrument (Stem Cell Technology).

Monocytes were differentiated into macrophages (Monocyte-Derived Macrophages, MDM) as follows. Purified CD14+ monocytes were cultured for 7-10 days in hydrophobic Teflon dishes (Lumox; D Dutscher) in macrophage medium (RPMI 1640 supplemented with 200 mM L-glutamine, 10 IU/mL penicillin, 10 µg/mL streptomycin, 10 mM HEPES, 10 mM sodium pyruvate, 50 µM β-mercaptoethanol, 1% minimum essential medium, vitamins, 1% nonessential amino acids) supplemented with 15% human AB serum. For experiments, macrophages were harvested and resuspended in macrophage medium containing 10% heat-inactivated FCS.

Purified CD4+ cells were stimulated for 3 days with PHA at 1 µg/mL or concanavalin A at 10 µg/ml in the presence of IL-2 (Chiron) at 100 IU/mL. The culture medium was RPMI 1640 containing 10% FCS, penicillin (10 IU/mL) and streptomycin (10 µg/mL).

HIV-1 and SIVmac251 Infection

Human macrophages and activated CD4+ T cells ($10^6$ cells/mL) were infected in vitro with productive HIV-1 BaL (R5), primary isolate HIV-1 BX08 (genebank accession number AY713411) or with single cycle HIV-1 particles produced by cotransfecting (SuperFect; QIAGEN) 293T cells with Vesicular stomatitis virus glycoprotein (VSV-G)-pseudotyped HIV-1 NL4.3Δenv particles carrying the GFP reporter gene. Macaque cells were infected with SIVmac251 as previously described [8]. Cells were infected in 96-U-well plates with a spinoculation protocol.

For productive infections, the cells were washed after challenge and cultured in 96-U-well plates ($10^6$ cells/mL in triplicate) for 3 days. Viral HIV-1 and SIVmac replication was were monitored by measuring p24 or p27, respectively, in the supernatant with an ELISA method at the end of the culture (Zeptometrix) or by flow cytometry.

For single cycle infections, CD4+ T cells were washed after challenge and cultured for three days. At the end of the culture, cells were harvest, washed and, after labelling for cell viability (see below), the cells were fixed in 1% paraformaldehyde. The percentage of infected cells was evaluated as the frequency of cells expressin GFP after flow cytometry on an LSRII device (BD Bioscience).

Apoptosis and Cell Viability Analysis

Detection of phosphatidylserine on apoptotic cells was performed by using an AnnexinV/propidium iodide (PI) detection kit (Beckman Coulter, Immunotech, Marseille, France) according to the manufacturer. Briefly, 5×105 cells were incubated in the dark at 4° C. with Annexin V-fluorescein isothiocyanate (FITC) and 2.5 µg/mL PI in phosphate buffer for 10 minutes before 18 000 ungated events were collected within the hour by flow cytometry (FACScalibur, BD Biosciences, Mansfield, Mass.) and analyzed with the ProCellQuest software provided by the manufacturer. In HIV-1 infection assays (see below), cell viability was determined with the help of LIVE/DEAD® Fixable Aqua stain kit as recommended by the manufacturer (Molecular Probes, Life Technologies, Saint Aubin, France).

Quantitative RT-PCR Analysis of AAC-11 mRNA Expression

Total RNA was extracted from activated CD4+ T lymphocytes, at the time of infection and 24-48 h after infection with VSV-G-pseudotyped HIV-1, with the RNeasy kit (QIAGEN) and treated with DNase, following the manufacturer's instructions. AAC-11 RNA was quantified with the GeneQuant method (Amersham) and reverse transcribed with SuperScript II reverse transcriptase (Invitrogen). The amplification program consisted of 10 minutes at 25° C., 50 minutes at 42° C., and 15 minutes at 70° C. PCR amplification of cDNA was performed in duplicate in MicroAmp Optical 96-well reaction plates (30 µL/well), using 15 µL of TaqMan Universal Master Mix, 0.2 mM TaqMan, and 1.5 µL of Assays-on-Demand Gene Expression Assay premade mix (GAPDH, Hs99999905_m1; AAC-11, Hs; Applied Biosystems). The amplification conditions were as follows: 50° C. for 2 minutes and 95° C. for 10 minutes followed by 40 cycles at 95° C. for 15 seconds and 60° C. for 60 seconds on an ABI PRISM 7000 Sequence Detection System (Applied Biosystems). The amount of target mRNA in each sample was normalized to GAPDH mRNA as an endogenous reference, and the data were analyzed with the cycle threshold (Ct) method.29 All results were expressed relative to a control cDNA, obtained from CD4+ T cells of a healthy donor, as 2-ΔΔCt, where ΔΔCt=ΔCtSAMPLE−ΔCtCONTROL, and ΔCt=CtTARGET GENE−CtGAPDH.

Results

Apoptosis is a fundamental biological process of programmed cell death that plays a critical role in the normal development of multicellular organisms, cellular differentiation and in maintaining tissue homeostasis. Moreover, apoptosis has been demonstrated as an important mechanism for viral clearance. There are numerous evidences indicating that virus modulates the apoptotic machinery as well as the cellular stress responses during the course of infection and as the associated disease progresses, and prevention of host cell death from apoptosis and stress cell response favors viral persistence.

The survival protein AAC-11 (Antiapoptosis clone-11, also known as Api5, for apoptosis inhibitor 5) is an ubiquitously expressed 55 kDa nuclear protein whose expression prevents apoptosis triggered by growth factor deprivation [1, 2]. AAC-11 has previously been shown to be overexpressed in multiple cancer cells and contribute to tumor invasion and metastases [3]. Our data and others have shown AAC-11 is critically involved in tumor survival, through inhibition of apoptosis [2, 4]. Interestingly, silencing of AAC-11 sensitizes tumor cells to chemotherapeutic drugs or various stress conditions, whereas its overexpression drastically increases tumor cells migration and invasiveness [2, 5]. Very recently, AAC-11 has been identified as a novel immune escape gene in tumors that promotes immune resistance to antigen-specific T cells [6]. Therefore, these data indicate that AAC-11 should be involved in the emergence and development of cancer, conferring resistance to induced or spontaneous cell death, protection against apoptosis and cellular stress, and capacity of metastasis.

Various components of multiprotein complexes have been identified as AAC-11-interacting protein partners, suggesting that AAC-11 may act as a scaffold for multiprotein complexes. Our results and other' indicate that expression of AAC-11 is induced by a number of cell stress conditions, including hypoxia, hyperthermia, oxidative stress, DNA damage and growth factors withdrawal. Interestingly, depletion of AAC-11 is lethal for cancer cells under conditions of low-serum stress [4]. These observations suggest that AAC-11 could function as intracellular stress sensor, mediating its activity through a complex interplay of physical interactions with other cellular proteins that are implicated in cellular survival, cell cycle regulation and the response of cells to stress, and these stress response functions may be targeted using AAC-11 inactivating strategies.

The LZ domain of AAC-11 is crucial for its biological functions, probably by acting as a protein-protein interaction module [1, 2]. Therefore, targeting the LZ of AAC-11 might prevent its binding to the protein partners, thus inhibiting AAC-11 function as signal transducer.

The inventors have developed cell penetrating peptides derived from the LZ of AAC-11 that disrupt protein-protein interactions between AAC-11 and its partners, thus resulting in its inactivation [2, 3]. Interestingly, these peptides selectively disrupt vital cellular functions in a plurality of cancer cells, but not normal cells, including blood cells from healthy donors, exposed to multiple cellular stresses at low or sub-micromolar range.

In the context of viral infections, the virus must control apoptosis and cellular stress responses induced as a defensive mechanism by the infection itself. However, viruses have evolved mechanisms to influence the balance of death and survival of the host cell in order to promote efficient virus replication and persistence of infection. Tilting this delicate balance by drug-induced enhancement of virus mediated cytotoxicity could potentially be exploited as a means for rapid elimination of infected cells.

HIV-1 induces and relies on cell stress response to complete its replication cycle. The inventors described that induction of AAC-11 integrate the HIV-induced stress response and that this provide a means to tackle HIV infection by targeting of AAC-11 and selective elimination of the infected cells. The inventors have found that indeed HIV infection is dependent on the expression of AAC-11; and therefore, inhibition of this protein inhibits both the infection and the production of virus progeny. Further exploration of AAC-11 expression during viral infection led to the inventors' discovery that AAC-11 accumulates at elevated levels after infection of cells with HIV. Therefore, according to the invention, inhibition of AAC-11 is useful for the elimination of the HIV infected cells and to counteract viral infections.

The compounds of the invention target a cellular protein that is expressed under circumstances of stress, rather than a viral component, to counteract viral infection. Most current antivirals target a viral component, which often results in the appearance of drug-resistant virus mutants. Resistance to the compounds of the invention, that target a cellular gene, is unlikely to arise by mutations in the virus genome. Further, as AAC-11 gives the infected cells a survival benefit during both infection and viral replication, through inhibition of apoptosis and the cell stress response, which are common to most if not all virus infections, inhibitors of AAC-11 are likely to be broad-spectrum antivirals. The inventors have found that inhibition of AAC-11 also blocks SIVmac infection of macaque CD4+ T cells.

Amino Acid Sequences:

```
Amino acid sequence of Penetratin-lined AAC-11
LZ-derived peptides:
AAC-11-LZ (363-399):
                                           SEQ ID NO: 2
AKLNAEKLKDFKIRLQYFARGLQVYIRQLRLALQGKT AAC-11-LZ (377-399):
                                           SEQ ID NO: 3
LQYFARGLQVYIRQLRLALQGKT Antp-AAC-11-LZ (363-399) (RT53):
                                           SEQ ID NO: 4
RQIKIWFKKQNRRMKWKKAKLNAEKLKDFKIRLQYFARGLQVYIRQLRL
ALQGKT Antp-AAC-11-LZ (377-399) (RT39):
                                           SEQ ID NO: 5
RQIKIWFKKQNRRMKWKKLQYFARGLQVYIRQLRLALQGKT Antp-AAC-11-LZ (379-391) (RL29):
                                           SEQ ID NO: 6
RQIKIWFKKQNRRMKWKKYFARGLQVYIRQL Cell-penetrating peptides:
Penetratin (Antp):
                                           SEQ ID NO: 7
RQIKIWFKKQNRRMKWKK Transactivator of Transcription cell penetrating
sequence (TAT 47-57):
                                           SEQ ID NO: 8
YGRKKRRQRRR
```

REFERENCES

Throughout this application, various references describe the state of the art to which this invention pertains. The disclosures of these references are hereby incorporated by reference into the present disclosure.

1. Tewari, M., et al., AAC-11, a novel cDNA that inhibits apoptosis after growth factor withdrawal. Cancer Res, 1997. 57(18): p. 4063-9.
2. Rigou, P., et al., The antiapoptotic protein AAC-11 interacts with and regulates Acinus-mediated DNA fragmentation. Embo J, 2009. 28(11): p. 1576-88.
3. Hou, J., et al., Expression profiling-based subtyping identifies novel non-small cell lung cancer subgroups and implicates putative resistance to pemetrexed therapy. J Thorac Oncol, 2012. 7(1): p. 105-14.
4. Morris, E. J., et al., Functional identification of Api5 as a suppressor of E2F-dependent apoptosis in vivo. PLoS Genet, 2006. 2(11): p. e196.
5. Kim, J. W., et al., AAC-11 overexpression induces invasion and protects cervical cancer cells from apoptosis. Lab Invest, 2000. 80(4): p. 587-94.
6. Ariazi, E. A., et al., Estrogen induces apoptosis in estrogen deprivation-resistant breast cancer through stress responses as identified by global gene expression across time. Proc Natl Acad Sci USA, 2011. 108(47): p. 18879-86.
7. Ramana L N, Anand A R, Sethuraman S, Krishnan U M. Targeting strategies for delivery of anti-HIV drugs. J Control Release. 2014 Oct. 28; 192:271-83.
8. Bruel, H., et al., Long-term control of simian immunodeficiency virus (SIV) in cynomolgus macaques not associated with efficient SIV-specific CD8+ T-cell responses. J Virol, 2015. 89(7) p. 3542-56

The invention claimed is:

1. A method for treating a viral an HIV infection in a subject in need thereof, comprising the step of administering to said subject a therapeutically effective amount of an AAC-11 inhibitor compound to treat said viral HIV infection, wherein said AAC-11 inhibitor compound is a polypeptide comprising or consisting of i) an amino acid sequence ranging from the phenylalanine residue at position 379 to the leucine residue at position 391 in SEQ ID NO:1 or, ii) an amino acid sequence having at least 70% identity with the amino acid sequence ranging from the phenylalanine residue at position 379 to the leucine residue at position 391 in SEQ ID NO:1, or iiii) an amino acid sequence which is a retro-inverso of the amino acid sequence ranging from the phenylalanine residue at position 379 to the leucine residue at position 391 in SEQ ID NO:1 or, iv) an amino acid sequence which is retro-inverso of the amino acid sequence having at least 70% identity with the amino acid sequence ranging from the phenylalanine residue at position 379 to the leucine residue at position 391 in SEQ ID NO:1.

2. The method according to claim 1 wherein said AAC-11 inhibitor compound is a fusion protein comprising the polypeptide fused to at least one heterologous polypeptide.

3. The method according to claim 2 wherein the at least one heterologous polypeptide is a cell-penetrating peptide.

\* \* \* \* \*